(12) United States Patent
Li et al.

(10) Patent No.: US 8,304,540 B2
(45) Date of Patent: Nov. 6, 2012

(54) PROCESS FOR STEREOSELECTIVE SYNTHESIS OF LAMIVUDINE

(75) Inventors: Jinliang Li, Shanghai (CN); Feng Lv, Shanghai (CN)

(73) Assignee: Shanghai Desano Pharmaceutical Holding Co., Ltd., Shanghai (CN)

( * ) Notice: Subject to any disclaimer, the term of this patent is extended or adjusted under 35 U.S.C. 154(b) by 392 days.

(21) Appl. No.: 12/619,830

(22) Filed: Nov. 17, 2009

(65) Prior Publication Data

US 2010/0063283 A1 Mar. 11, 2010
US 2010/0249409 A2 Sep. 30, 2010
US 2011/0118465 A2 May 19, 2011

Related U.S. Application Data

(63) Continuation of application No. PCT/CN2007/002038, filed on Jun. 29, 2007.

(30) Foreign Application Priority Data

May 18, 2007 (CN) .......................... 2007 1 0040912

(51) Int. Cl.
  *C07D 411/04* (2006.01)

(52) U.S. Cl. ....................................................... 544/317
(58) Field of Classification Search ................... 544/317
  See application file for complete search history.

(56) References Cited

U.S. PATENT DOCUMENTS 6,051,709 A 4/2000 Goodyear et al.
6,329,522 B1 12/2001 Hill et al.

FOREIGN PATENT DOCUMENTS

CN 1149871 5/1997
CN 1321641 11/2001
CN 1618795 5/2005

OTHER PUBLICATIONS

Li et al., CAPLUS Abstract 138:106682 (2003).*
Yuan, CAPLUS Abstract 144:412836 (2006).*

* cited by examiner

*Primary Examiner* — Deepak Rao
(74) *Attorney, Agent, or Firm* — Dorsey & Whitney LLP

(57) ABSTRACT

The present invention discloses a process for stereoselective synthesis of Lamivudine comprising the following steps: (a) performing a glycosylation reaction between the compound of formula (I) and cytosine or protected cytosine, and separating the reaction product by recrystallization to obtain the intermediate of formula (II); and (b) deprotecting the intermediate of formula (II) to obtain Lamivudine.

11 Claims, No Drawings

PROCESS FOR STEREOSELECTIVE SYNTHESIS OF LAMIVUDINE

CROSS REFERENCE TO RELATED APPLICATIONS

This application is a continuation of International Patent Application No. PCT/CN2007/002038, filed on Jun. 29, 2007, which claims priority to Chinese Patent Application No. 200710040912.1, filed on May 18, 2007, the entire contents of both of which are incorporated herein by reference.

TECHNICAL FIELD

The present application relates to a process for stereoselective synthesis of Lamivudine.

BACKGROUND OF THE INVENTION

Lamivudine is a nucleoside reverse transcriptase inhibitor, and is a kind of deoxycytidine analogue, which can inhibit the reproduction of Human immunodeficiency virus (HIV) and hepatitis B virus (HBV), whose chemical name is (2R-cis)-4-amino-1-(2-hydroxymethyl-1,3-oxathiolan-5-yl)-1H-pyrimidin-2-one, and structural formula is as follows:

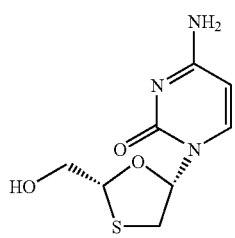

In 1990, Belleau et al firstly reported Lamivudine structure, and BioChem Pharma of Canada firstly developed Lamivudine to be used to treat AIDS (WO91/17159) and hepatitis B (EP0474119), and found that it had distinguished therapeutic effect on hepatitis B. Since Lamivudine has two chiral centers, it has 4 stereisomers, among which the 2R,5S (2R-cis)-isomer is the most potent in anti-HIV and anti-HBV activities, and its cytotoxicity on some cells is lower than its enantiomer or racemic body.

WO94/14802 mentioned two synthetic schemes (see Scheme 1 and Scheme 2):

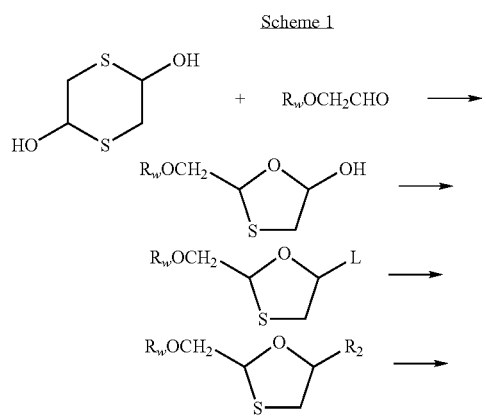

Scheme 1

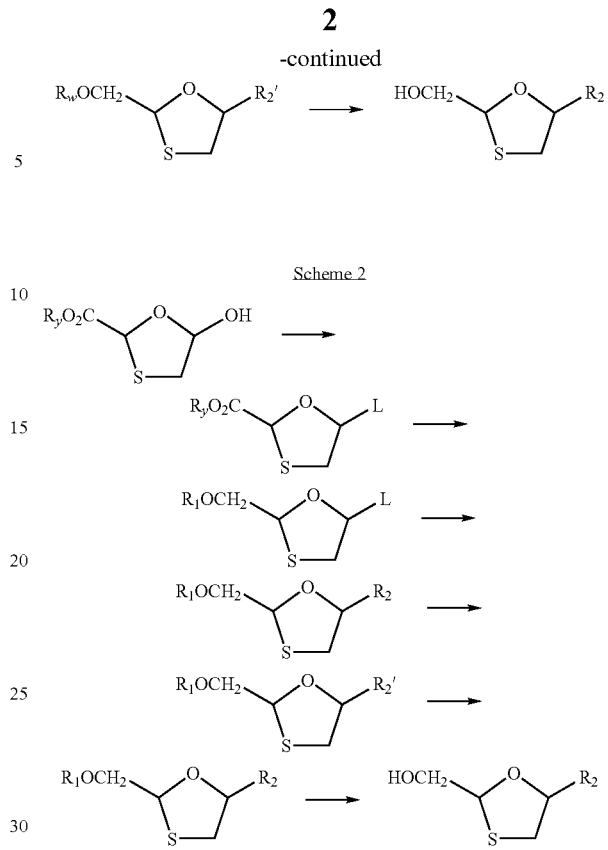

Scheme 2

In the above two schemes of this process, chirality was not controlled, and the final product was obtained by column chromatography, thus the yield was low and the requirement on the equipment was high, resulting in that the production cost was high and the operation in the production could not be controlled easily.

SUMMARY OF THE INVENTION

The technical problem to be solved by the present invention is to provide a process for stereoselective synthesis of Lamivudine to overcome the deficiencies existing in the above techniques.

The technical concept of the present invention is as follows:

In order to obtain Lamivudine of high optical purity, it is assumed in the present invention that before the glycosylation reaction, the configuration of position 2 (R-configuration) of Lamivudine is fixed then the glycosylated products will only include a pair of diastereomers, which can be separated easily by the skilled in the art. It is proved by studies that this pair of diastereomers can be separated by recrystallization only.

The process for stereoselective synthesis of Lamivudine according to the present invention comprises the following steps:

(a) performing a glycosylation reaction between the compound of formula (I) and cytosine or protected cytosine, and separating the reaction product by recrystallization to obtain the intermediate of formula (II); and (b) deprotecting the intermediate of formula (II) to obtain Lamivudine, The specific reaction scheme is as follows:

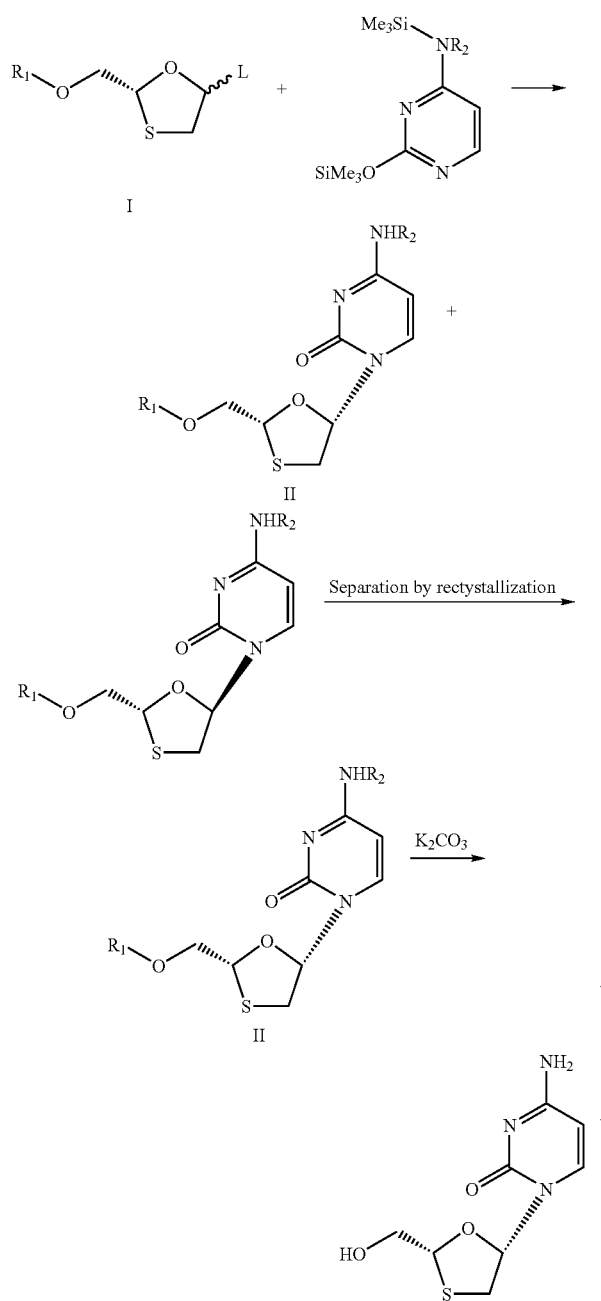

wherein R₁ is a hydroxyl protecting group containing a chiral center, L is a leaving group; and R₂ is hydrogen or an amino protecting group.

In a preferred example of the present invention, preferably, R₁ is L-mentholformyl; L is methoxy or halogen or acetate group; and preferably, R₂ is hydrogen or acetyl.

In a preferred example of the present invention, step (a) can be specifically described as follows: cytosine or 4-amino protected cytosine is reacted with hexamethyldisilazane to give silylated 4-amino protected cytosine; which is then reacted with the compound of formula (I) at 10-80° C. for 1-20 hours; finally, the resulting glycosylated product is separated by recrystallization to give 2R,5S-intermediate of formula (II) of high optical purity.

The 4-amino protected cytosine is $N^4$-acetylcytosine.

In another preferred example of the present invention, the recrystallization separation in step (a) is performed by a solvent.

The solvent is preferably an alcohol. The alcohol is preferably ethanol. Of course, the solvent is not limited to an alcohol, as long as it will not destroy the glycosylated product and can efficiently recrystallize and separate the diastereomers.

In a preferred example of the present invention, step (b) can be specifically described as follows: the intermediate of formula (II) from step (a) is hydrolyzed by a base, and forms a salt with an organic acid; then the salt precipitates from water and finally the water insoluble salt is neutralized by an organic base to give Lamivudine.

The organic acids include, but not limited to p-nitrobenzoic acid.

In a preferred example of the present invention, the synthetic route is preferably as follows:

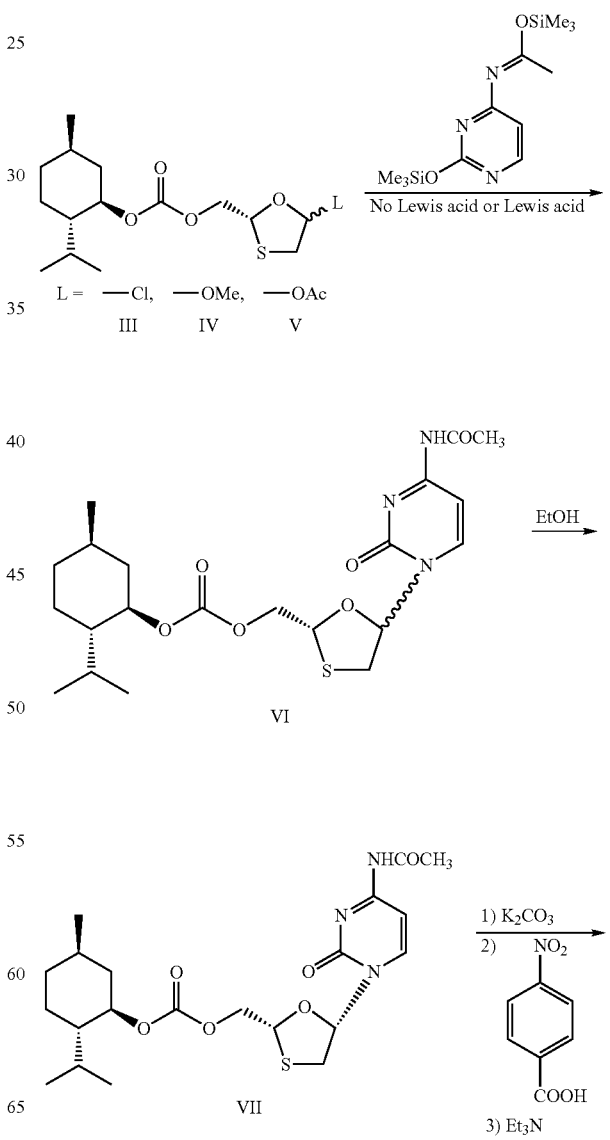

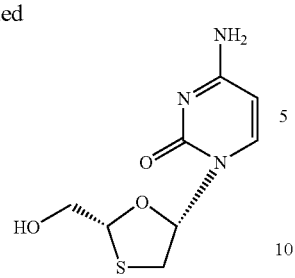

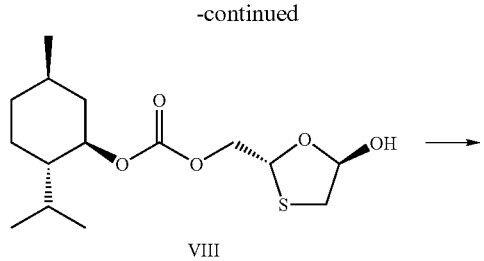

In a preferred example of the present invention, the preparation method of the compound of formula (I) is as follows: the chiral auxiliary menthol is acylated by triphosgene to give L-menthol chloroformate, which is reacted with 1,2-isopropylidene protected glycerol, and then hydrolyzed to deprotect 1,2-isopropylidene; then the resulting product is oxidized by sodium periodate, and condensed with 1,4-dihydroxy-2,5-dithiane to give an intermediate of formula (VIII) of high optical purity; and, a hydroxyl at position 5 of the intermediate of formula (VIII) is substituted by chlorine to give a compound of formula (III), which belong to the compound of formula (I). The specific reaction scheme is as follows:

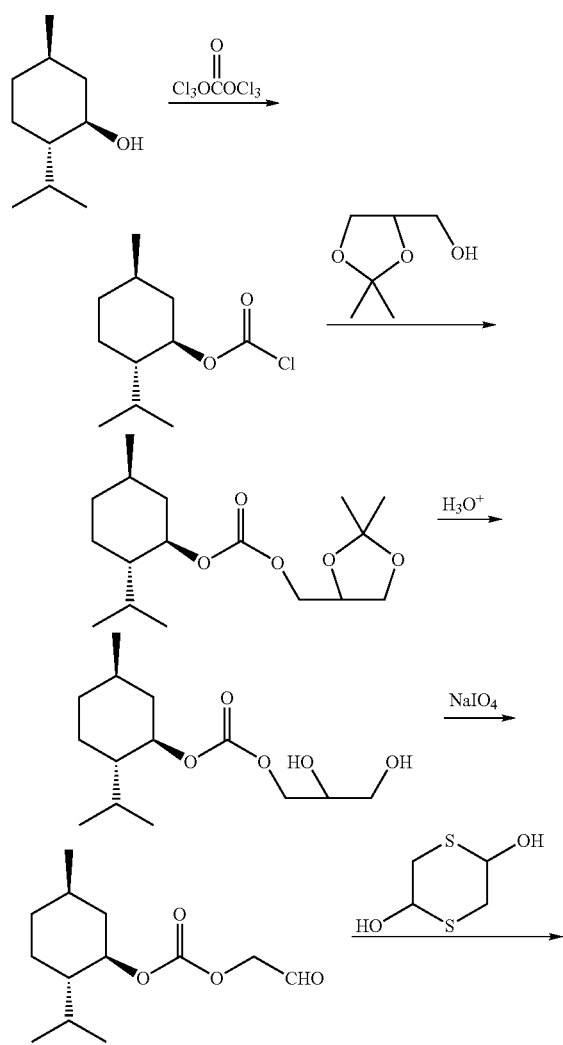

wherein X is Cl or Br.

In a preferred example of the present invention, the preparation method of the compound of formula (I) may also be as follows: a chiral compound of formula (IX) reported in WO95/29174 is used as a starting material, and methyl etherificated at 5-hydroxy, then reduced to give the intermediate of formula (X), then a chiral auxiliary is introduced to the hydroxy at position 2 of the intermediate of formula (X) to obtain the compound of formula (I). The specific reaction scheme is as follows:

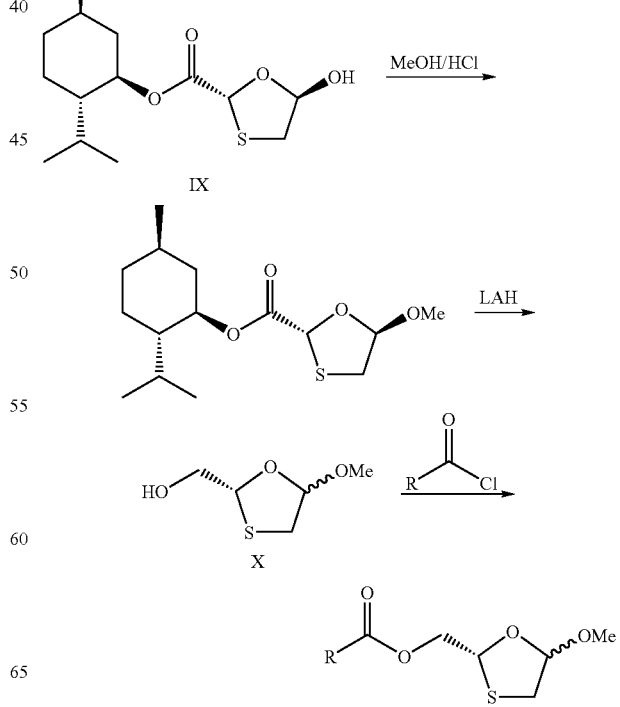

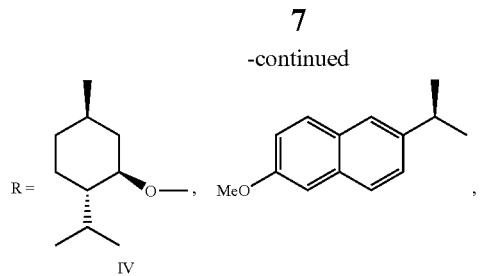
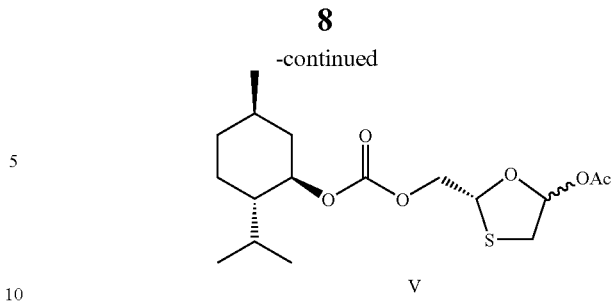

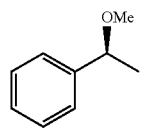

This preparation method has a certain chiral control on the next glycosylation reaction.

The said method for introducing a chiral auxiliary comprises esterificating the acyl compound containing the chiral auxiliary with the intermediate of formula (X).

After studying the introduced chiral auxiliary, we have found that the preferred acyl compounds containing the chiral auxiliary include, but not limited to one of L-menthol formyl chloride, (S)-naproxenoyl chloride and (R)-methyl mandeloyl chloride. It has been found in the studies that the chiral control ability of menthol is the best. Therefore, the acyl compound containing the chiral auxiliary is preferably L-menthol formyl chloride.

In order to enhance the yield of the glycosylation reaction, the intermediate of formula (N) for chiral control can be transformed to a compound of formula (V), which then undergoes a glycosylation reaction with protected cytosine. In this manner, the expensive trifluoromethanesulfonic acid trimethylsilanol ester (a Lewis acid catalyst) can be replaced by trimethyliodosilane which is much cheaper, thus greatly reducing the cost of the starting materials. The reaction scheme is as follows:

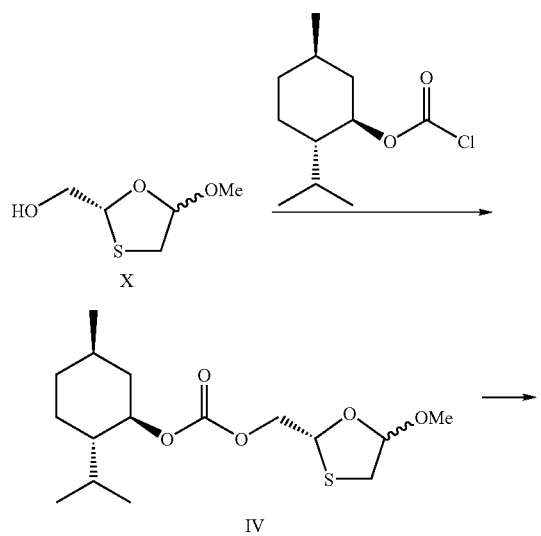

By using the above process to produce Lamivudine, the product assay can reach above 99%, and the amount of its enantiomer is not high than 0.2%. The HPLC and chiral HPLC analytic methods can use the method as described in United States Pharmacopoeia USP29.

The present process has the following advantages: the reaction condition is mild, the stereoselectivity of the intermediate is high, the diastereomer can be separated by simple recrystallization, and the operation is simple and suitable for industrial production.

MODE FOR CARRYING OUT THE INVENTION

The present invention is further illustrated in detail by the Examples.

EXAMPLE 1

The preparation of L-menthol chloroformate

Under a nitrogen atmosphere, triphosgene (314.9 g, 1.19 mol) and toluene (6 L) were added to a reaction flask, and stirred to make triphosgene totally dissolved in toluene. At −10° C., L-menthol (546.5 g, 3.50 mol) was added, and stirred to make it dissolved in the above mixture, and then pyridine (451.0 g, 3.50 mol) was added dropwise. After the addition was complete, the reaction was conducted for 2 hours at that temperature. The reaction liquid was washed by water thrice (50 ml×3), the organic layer was dried by anhydrous sodium sulfate, and the solvent was evaporated under normal atmosphere to obtain oil, which was distilled under reduced pressure (5 mmHg). The fraction of 90-93° C. was collected to obtain the title compound, and the yield was 75%.

EXAMPLE 2

(2,2-dimethyl-1,3-dioxolan-4-yl)-methyl-(1R,2S,5R)-2-isopropyl-5-methyl cyclohexyl carbonic acid diester At 0° C., L-menthol chloroformate (2.2 g, 0.01 mol), (2,2-dimethyl-1,3-dioxolan-4-yl)-methanol (2.2 g, 0.01 mol), N,N-dimethylamino pyridine (0.1 g, 1.0 mmol) and dichloromethane (15 ml) were added to a reaction flask. Triethylamine (3.2 g, 0.03 mol) was slowly added under vigorous stirring. After the addition was complete, the mixture was stirred for 0.5 hour, after which the reaction was stopped. The organic layer was washed by saturated sodium bicarbonate and water and then the solvent was evaporated. The crude product was purified by a silica gel column (eluted by ethyl acetate:petroleum ether=1:10), to give 2.4 g of the title compound, and the yield was 76%. 1H-NMR (CDCl$_3$) δ: 4.50 (m, 1H), 4.32 (m, 1H), 4.25 (m, 2H), 4.15 (m, 1H), 3.80 (m, 1H), 2.11 (m, 1H), 2.00 (m, 1H), 1.70 (m, 2H), 1.50 (m, 2H), 1.44 (s, 3H), 1.42 (s, 3H), 1.28 (m, 1H), 1.11 (m, 2H), 0.9 (m, 6H), 0.82 (d, 3H). Elemental analysis: C17H30O5 found (%): C, 64.97; H, 9.60; O, 25.43; calculated (%) C, 64.94; H 9.62; O, 25.44.

EXAMPLE 3

2,3-dihydroxypropyl-(1R,2S,5R)-2-isopropyl-5-methyl cyclohexyl carbonic acid diester The compound of Example 2 (3.1 g, 0.01 mol), p-toluene sulfonic acid monohydrate (0.2 g, 0.001 mol) and methanol (20 ml) were added to a reaction flask, and then the mixture was stirred at room temperature for 7 hours, after which, the reaction was stopped and the reaction mixture was washed by saturated sodium carbonate aqueous solution. The solvent was evaporated from the organic layer and the crude product was purified by a silica gel column (eluted by ethyl acetate: petroleum ether=1:6) to give 2.5 g of the title compound, and the yield was 90%. 1H-NMR (CDCl$_3$) δ: 4.50 (m, 1H), 4.32~4.09 (m, 2H), 3.91~4.00 (m, 1H), 3.5~03.75 (m, 2H), 2.11 (m, 1H), 2.00 (m, 1H), 1.70 (m, 2H), 1.50 (m, 2H), 1.28 (m, 1H), 1.11 (m, 2H), 0.9 (m, 6H), 0.82 (d, 3H). Elemental analysis: C14H26O5 found (%): C, 61.32; H, 9.54; O, 29.14; calculated (%) C, 61.29; H, 9.55; O, 29.16.

EXAMPLE 4

(1R,2S,5R)-2-isopropyl-5-methy cyclohexyl-2-oxo-ethyl carbonic acid diester

The compound of Example 3 (2.7 g, 0.01 mol), silica gel (1 g) and acetone (20 ml) were added to a reaction flask, and then an aqueous solution (10 ml) of sodium periodate (2.3 g, 0.011 mol) was added under vigorous stirring. The mixture was further stirred for 8 hours, and then the reaction was stopped and filtered. The solvent was evaporated from the organic layer and the crude product was purified by a silica gel column (eluted by ethyl acetate:petroleum ether=1:6) to give 2.1 g of the title compound, and the yield was 87%. $^1$H NMR (CDCl$_3$) δ: 9.66 (s, 1H), 4.67 (s, 2H), 4.50 (m, 1H), 2.11 (m, 1H), 2.00 (m, 1H), 1.70 (m, 2H), 1.50 (m, 2H), 1.28 (m, 1H), 1.11 (m, 2H), 0.9 (m, 6H), 0.82 (d, 3H). Elemental analysis: C13H22O4 found (%): C, 64.45; H, 9.17; O, 26.38; calculated (%) C, 64.44; H, 9.15; O, 26.41.

EXAMPLE 5

The preparation of (2R,5R)-5-hydroxy-1,3-oxathiolane-2-methyl-(2'S-isopropyl-5'R-methyl-1'R-cyclohexyl)-carbonic acid diester of formula (VIII)

Under a nitrogen atmosphere, the compound of Example 4 (24.2 g, 0.1 mol), 2,5-dihydroxy-1,4-dithiane (8.4 g, 0.11 mol) and tetrahydrofuran (100 mL) were mixed together and dissolved by stirring. At 0° C., BF$_3$.Et$_2$O (1.6 g, 0.011 mol) was added and then the mixture was further stirred for 0.5 hour, after which the mixture was reacted at room temperature for 16 hours. The reaction liquid was poured into 1 L of water and then extracted by ethyl acetate. The organic layer was dried and the solvent was evaporated. N-hexane and a small amount of triethylamine were added to the residues and then the residue was kept at a low temperature for a period, after which solids precipitated out. The solids were filtered, and dried to give 22.9 g of a whiter powder, i.e. the compound of formula (VIII), and the yield was 72%. 1H-NMR (CDCl$_3$) δ: 4.90 (m, 1H), 4.69 (d, 2H), 4.52 (m, 1H), 4.49 (m, 1H), 2.76 (d, 2H), 2.11 (m, 1H), 2.00 (m, 1H), 1.70 (m, 2H), 1.50 (m, 2H), 1.28 (m, 1H), 1.11 (m, 2H), 0.9 (m, 6H), 0.82 (d, 3H).

EXAMPLE 6

The preparation of (2R)-5-chloro-1,3-oxathiolane-2-carboxylic acid-(2'S-isopropyl-5R-methyl-1'R)cyclohexanol ester (III)

The compound of Example 5 (31.8 g, 0.1 mol) and dichloromethane (250 ml) were added to a reaction flask, and stirred to make the compound completely dissolved in dichloromethane. DMF (11.2 ml, 0.15 mol) was added and the reaction liquid was cooled to 0° C., and then thionyl chloride (7.7 ml, 0.11 mol) was added dropwise. The resulting solution was stirred at 10-15° C. for 2 hours, and the reaction liquid could be directly used in the next reaction.

EXAMPLE 7

The preparation of (2R,5S)-5-(4"-amino-2"-oxo-pyrimidin-1"-yl)-1,3-oxathiolane-2-methyl-(2'S-isopropyl-5'R-methyl-1'R-cyclohexyl)-carbonic acid diester of formula (VII)

(1) The Preparation of Silylated Acetylcytosine Solution

Cytosine (15.3 g, 0.1 mol), methanesulfonic acid (0.03 ml), hexamethyldisilazane (17.8 g, 0.11 mol) and dichloromethane (70 ml) were added to a reaction flask and heated under reflux. After the solution was transparent, the silylated cytosine solution was obtained.

(2) The preparation of (2R,5S)-5-(4"-acetamido-2"-oxo-pyrimidin-1"-yl)-1,3-oxathiolane-2-methyl-(2'S-isopropyl-5'R-methyl-1'Rcyclohexyl)-carbonic acid diester of formula (VII)

Triethylamine (14.5 mL, 0.11 mol) was added to a prepared silylated cytosine solution and then the reaction liquid was heated under reflux. The reaction solution of Example 6 was added slowly drop by drop. After the addition was complete, the reaction was further refluxed for 10 hours. After the reaction was complete, the reaction liquid was poured into water and the organic layer was washed by saturated ammonium sulphate aqueous solution and saturated brine and dried by anhydrous sodium sulfate. After the solvent was evaporated under reduced pressure, the residue was recrystallized by ethyl acetate and petroleum ether (V/V=1:5) to give 34.1 g of a mixture of white solid of formula (VI), and the yield was 75%. The ratio of α to β isomers was 1:1.5.

The mixture of α and β isomers of formula (VI) (34.1 g, 0.06 mol) was added to 500 ml of ethanol and then heated to reflux. After refluxed for 0.5 hour, the reaction mixture was cooled to room temperature. After stood for one day, the mixture was filtered to give a white solid, which was recrystallized by ethanol to give 8.0 g of the title compound, and the yield was 35%. 1H-NMR (CDCl$_3$) δ: 7.80 (d, 1H), 7.42 (d, 1H), 6.42 (m, 1H), 4.69 (d, 2H), 4.52 (m, 1H), 4.49 (m, 1H), 2.76 (d, 2H), 2.11 (m, 1H), 2.00 (m, 1H), 1.70 (m, 2H), 1.50 (m, 2H), 1.28 (m, 1H), 1.11 (m, 2H), 0.9 (m, 6H), 0.82 (d, 3H).

EXAMPLE 8

The preparation of (2R,5S)-4-amino-1-(2-hydroxymethyl-1,3-oxathiolane-5-yl)-2(1H)-pyrimidone (Lamivudine)

The compound of Example 7 (41.0 g, 0.1 mol) and methanol (250 ml) were added to a reaction flask, and then stirred to make the compound dissolved in methanol. The mixture was cooled to 0° C., and then $K_2CO_3$ (41.2 g, 0.3 mol) was added. The mixture was further stirred at room temperature overnight and then was adjusted by 0.1N HCl to a pH of about 7. The mixture was filtered and the solvent was evaporated under reduced pressure from the filtrate, and then to the residue was added 150 ml of water. The aqueous layer was extracted by 150 ml of toluene (50 ml×3), and then p-nitrobenzoic acid (16.8 g, 0.1 mol) was added to the aqueous layer and refluxed for 30 minutes, after which, the reaction mixture was cooled and further stirred at 0-5° C. for 2 hours. Then the reaction mixture was filtered and dried to give 31.7 g of a white solid.

The resulting salt and anhydrous ethanol (120 ml) were added to a reaction flask, and warmed to 70-75° C. Triethylamine (12 ml) was added dropwise, and the reaction was conducted at that temperature for 2 hours. Then the mixture was cooled to 50° C., at which point ethyl acetate (150 ml) was added dropwise. After the addition was complete, the mixture was cooled to 10° C. and further stirred for 4 hours. The mixture was filtered to give 15.6 g of Lamivudine, and the yield was 68%. 1H-NMR (DMSO-d6) δ: 7.83 (dd, 1H), 7.17~7.23 (dd, 2H), 6.21 (t, 1H), 5.72 (dd, 1H), 5.29 (t, 2H), 5.16 (t, 1H), 3.70~3.74 (m, 2H), 3.32~3.43 (dd, 1H), 3.01~3.05 (dd, 1H); Elemental analysis: C8H11N3O3S found (%): C, 41.85; H, 4.88; N, 18.25; S, 13.94; calculated (%) C, 41.91; H, 4.84; N, 18.33; S, 13.99.

EXAMPLE 9

The preparation of (2R)-5-methoxy-1,3-oxathiolane-2-methyl-(2'S-isopropyl-5'R-methyl-1'Rcyclohexyl)-carbonic acid diester The compound of formula (IX) (prepared according to WO95/29174) (2.00 Kg, 6.93 mol) and 1% HCl methanol solution (10 L) were added to a reaction flask. The reaction mixture was stirred at room temperature for 3 hours. 1.8 L of triethylamine was added, and the solvent was evaporated under reduced pressure. The crude product was purified by a silica gel column to give 1.05 Kg of the title compound, and the yield was 55%. $^1$H NMR (CDCl$_3$): δ 5.57, 5.50 (2×s, 1H, H-2), 4.75-4.62 (m, 1H, H-5), 3.50, 3.41 (2×s, 3H, CH$_3$O), 3.25-3.03 (m, 2H, H-4), 1.68-1.01 (m, 9H, H-menthyl), 1-0.93 (m, 7H H of CH—(CH$_3$)$_2$), 0.86-0.82 (s, 3H, CH$_3$ of menthyl).

EXAMPLE 10

The preparation of (2R)-5-methoxy-1,3-oxathiolane-2-methanol of formula (X)

Under a nitrogen atmosphere, lithium aluminum hydride (270 g, 7.12 mol), and 2 L of anhydrous tetrahydrofuran were added to a reaction flask. At 0° C., a solution of the compound of Example 9 (1.05 Kg, 3.47 mol) in tetrahydrofuran was added dropwise. After the addition was complete, the reaction mixture was stirred for 2 hours and then was diluted by water and filtered. The solvent was evaporated under reduced pressure and the crude product was purified by a silica gel column to give 394 g of the title compound, and the yield was 75%. $^1$H NMR (CDCl$_3$): δ 5.46, 5.30 (m, 2H, H-2 and H-5), 3.89-3.75 (m, 2H, H-2'), 3.46, 3.42 (2×s, 3H, CH$_3$O), 3.27-3.08 (m, 2H, H-4), 2.43, 2.09 (2×s, 1H, OH).

EXAMPLE 11

The preparation of (2R)-5-methoxy-1,3-oxathiolane-2-carboxylic acid-(2'S-isopropyl-5R-methyl-1'R) cyclohexanol ester (IV)

The compound of formula (X) (394 g, 2.62 mol), pyridine (207 g, 2.62 mol) and 1.2 L of dichloromethane were added to a three-necked flask. At 0° C., L-menthol chloroformate (576 g, 2.62 mol) was added dropwise. After the addition was complete, the temperature was warmed to room temperature and the reaction was continued for 2 hours. After the reaction was completed, the reaction mixture was poured into ice water and further stirred for 20 minutes. The organic layer was separated and washed successively by water, saturated NaHCO$_3$, and saturated brine and then was dried with anhydrous MgSO$_4$. The solvent was evaporated under reduced pressure to obtain the crude product of the title compound, which could be used in the next reaction without further purification.

EXAMPLE 12

The preparation of (2R,5S)-5-(4"-acetamido-2"-oxo-pyrimidin-1"-yl)-1,3-oxathiolane-2-methyl-(2'S-isopropyl-5'R-methyl-1'Rcyclohexyl)-carbonic acid diester of formula (VII)

(1) The Preparation of Silylated Acetylcytosine Solution

Under a nitrogen atmosphere, N$^4$-acetylcytosine (433 g, 2.83 mol), hexamethyldisilazane (500 g, 3.10 mol) and 1 L of toluene were added to a reaction flask, and heated under reflux for 2 hours, at which point the reaction liquid became clear, and was cooled to room temperature.

(2) The preparation of (2R,5S)-5-(4"-acetamido-2"-oxo-pyrimidin-1"-yl)-1,3-oxathiolane-2-methyl-(2'S-isopropyl-5'R-methyl-1'Rcyclohexyl)-carbonic acid diester of formula (VII)

The solution (3 L) of the compound of Example 11 (780 g, 2.35 mol) in dichloromethane and trimethylsilyl triflate (1.9 L) were added to the above silylated acetylcytosine solution and reacted at room temperature for 12 hours. The reaction liquid was washed by saturated sodium bicarbonate and water and the organic layer was dried by anhydrous sodium sulfate. After the solvent was evaporated, the residue was recrystallized by methanol-water to give 639 g of a white solid mixture of formula (VI), and the yield was 60%. The ratio of a to isomers was 1:1.7.

The mixture of α and β isomers of formula (VI) (639 g, 1.41 mol) was added to 9 L of ethanol and heated under reflux. After refluxed for 0.5 hour, the reaction mixture was cooled to room temperature. After stood for one day, the mixture was filtered to give a white solid, which was recrystallized by ethanol to give 150 g of the title compound, and the yield was 40%.

EXAMPLE 13

The Preparation of Lamivudine

The compound of Example 12 (150 g, 0.33 mol), $K_2CO_3$ (138 g, 1.0 mol) and methanol (3 L) were added to a reaction flask. The mixture was stirred at 0° C. for 10 hours. After the reaction was complete, the mixture was adjusted by 0.1N HCl to have a pH of about 7. The mixture was filtered and the solvent was evaporated under reduced pressure from the filtrate, and then to the residue was added 450 ml of water. The aqueous layer was extracted by 450 ml of toluene (150 ml×3), and then p-nitrobenzoic acid (56 g, 0.33 mol) was added to the aqueous layer and refluxed for 30 minutes, after which, the reaction mixture was cooled and further stirred at 0-5° C. for 2 hours. Then the reaction mixture was filtered and dried to give 105 g of a white solid.

The resulting salt and anhydrous ethanol (400 ml) were added to a reaction flask, and warmed to a temperature of 70-75° C. Triethylamine (40 ml) was added dropwise, and the reaction was conducted at that temperature for 2 hours. Then the mixture was cooled to 50° C., at which point ethyl acetate (500 ml) was added dropwise. After the addition was complete, the mixture was cooled to 10° C. and further stirred for 4 hours. The mixture was filtered to give 57 g of Lamivudine, and the yield was 75%.

EXAMPLE 14

The preparation of (2R)-5-methoxy-1,3-oxathiolane-2-methyl-(6'-methoxy)-2'(S)-naphthyl isopropionate (S)-naproxen (5.5 g, 0.024 mol) and oxalyl chloride (18 ml) were added to a reaction flask and reacted at room temperature for 1 hour. The excessive oxalyl chloride was evaporated under reduced pressure to give (S)-6-methoxy-2-naphthyl isopropionyl chloride. The crude product was dissolved in 20 ml of chloromethane, and then was slowly added to a reaction liquid of the compound of formula (VI) (3.0 g, 0.02 mol), pyridine (3.2 g, 0.04 mol) and 50 ml of dichloromethane. The mixture was reacted at room temperature for 3 hours, at which point the reaction was stopped and filtrated. The filtrate was evaporated to dryness to give the title compound, which could be used in the next step without further purification.

EXAMPLE 15

The preparation of (2R)-5-(4"-acetamido-2"-oxopyrimidin-1"-yl)-1,3-oxathiolane-2-methyl-(6'-methoxy)-2'(S)-naphthyl isopropionate

(1) The Preparation of Silylated Acetylcytosine Solution

Under a nitrogen atmosphere, $N^4$-acetylcytosine (3.7 g, 0.024 mol), hexamethyldisilazane (4.8 g, 0.03 mol) and 6 ml of toluene were added to a reaction flask and heated under reflux for 2 hours, at which point the reaction liquid became clear and was cooled to room temperature.

(2) The preparation of (2R)-5-(4"-acetamido-2"-oxopyrimidin-1"-yl)-1,3-oxathiolane -methyl-(6'-methoxy)-2"(S)-naphthalene isopropionate At room temperature, to the solution of the above compound, the solution of the compound from Example 14 in dichloromethane (25 ml) and trimethylsilyl triflate (8.9 g, 0.04 mol) were added and reacted at room temperature for 12 hours. The reaction liquid was washed by saturated sodium bicarbonate and water and the organic layer was dried by anhydrous sodium sulfate. The solvent was evaporated and the crude product was recrystallized by methanol to give 45 g of the title compound, and the yield was 47%. $^1$H NMR ($CDCl_3$): δ 9.47 (s, 1H), 8.22 (dd, 1H), 7.46 (dd, 1H), 8.00-7.12 (m, 6H, H-phenyl), 6.34 (s, 1H), 5.41 (s, 1H,), 4.51-4.66 (m, 2H), 3.92 (s, 3H), 3.78 (m, 1H), 3.62-3.66 (dd, 1H), 3.20-3.23 (dd, 1H), 2.10 (s, 3H), 1.60 (d, 3H).

EXAMPLE 16

The Preparation of Lamivudine and its 5-Position Diastereomer

The compound of Example 15 (4.8 g, 0.01 mol) and 50 ml methanol were added to a reaction flask, and then $K_2CO_3$ (4.41 g, 0.03 mol) was added. The reaction mixture was reacted at room temperature overnight and filtered. The solvent was evaporated under reduced pressure and the crude product was purified by a silica gel column to give 2.0 g of Lamivudine and its 5-position diastereomer, and the yield was 88%. The ratio of α to β isomers was 1:1.1.

EXAMPLE 17

The preparation of (2R)-5-methoxy-1,3-oxathiolane-2-methyl-(2'(R)-methoxy)phenyl acetate The compound of formula (VI) (3.0 g, 0.02 mol), pyridine (3.2 g, 0.04 mol) and 50 ml of dichloromethane were added to a three-necked flask. At room temperature, the solution of (R)-methylmandelic acid (3.1 g, 0.024 mol) in dichloromethane (15 ml) was added slowly drop by drop. After the addition was complete, the reaction mixture was reacted at room temperature for 3 hours and then the reaction was stopped. The reaction mixture was filtered and the filtrate was evaporated to dryness to give the title compound, which could be used in the next step without further purification.

EXAMPLE 18

The preparation of (2R)-5-(4"-acetamido-2"-oxopyrimidin-1"-yl)-1,3-oxathiolane-2-methyl-(2'(R)-methoxy)phenyl acetate At room temperature, to a solution of the compound from step (1) of Example 15 was added a solution of the compound of Example 17 in dichloromethane (25 ml) and trimethylsilyl triflate (8.9 g, 0.04 mol) and then the reaction mixture was reacted at room temperature for 12 hours. The reaction liquid was washed by saturated sodium bicarbonate and water and the organic layer was dried by anhydrous sodium sulfate. The solvent was evaporated and the crude product was crystallized by methanol to give 5.7 g of the title compound, and the yield was 68%. 1H NMR ($CDCl_3$): δ 9.47 (s, 1H), 8.22 (dd, 1H), 7.46 (dd, 1H), 7.50-7.15 (m, 5H, H-phenyl), 6.34 (s, 1H), 5.52 (s, 1H) 5.41 (s, 1H,), 4.51-4.66 (m, 2H), 3.62-3.66 (dd, 1H), 3.26 (s, 3H), 3.20-3.23 (dd, 1H), 2.10 (s, 3H).

EXAMPLE 19

The Preparation of Lamivudine and its 5-Position Diastereomer

The compound of Example 18 (4.2 g, 0.01 mol) and 50 ml of methanol were added to a reaction flask, and then $K_2CO_3$ (4.4 g, 0.03 mol) was added. The reaction mixture was reacted at room temperature overnight and filtered. The solvent was evaporated under reduced pressure and the crude product was purified by a silica gel column to give 1.8 g of Lamivudine and its 5-position diastereomer, and the yield was 80%. The ratio of α to β isomers was 1:1.

EXAMPLE 20

The preparation of (2R)-5-methoxy-1,3-oxathiolane-2-methyl benzoate

The compound of formula (VI) (3.0 g, 0.02 mol), pyridine (3.2 g, 0.04 mol) and 50 ml of dichloromethane were added to a three-necked flask. At room temperature, benzoyl chloride (3.1 g, 0.024 mol) was added slowly drop by drop. After the addition was complete, the reaction mixture was reacted at room temperature for 3 hours and then the reaction was stopped. The reaction mixture was filtered and the filtrate was evaporated to dryness to give the title compound, which could be used in the next step without further purification. The product could be recrystallized with diethyl ether to give a white solid. 1H NMR (CDCl$_3$): 8.18-7.44 (m, 5H, H-phenyl), 5.64, 5.41 (m, 2H, H-2 and H-5), 4.58-4.43 (m, 2H, H-2'), 3.46, 3.42 (2×s, 3H, CH$_3$O), 3.27-3.08 (m, 2H, H-4).

EXAMPLE 21

The preparation of (2R,5S)-5-(4"-acetamido-2"-oxo-pyrimidin-1"-yl)-1,3-oxathiolane-2-methyl benzoate At room temperature, to a solution of the compound from step (1) of Example 15 was added a solution of the compound from Example 20 in dichloromethane (25 ml) and trimethyl-silyl triflate (8.9 g, 0.04 mol) and then the reaction mixture was reacted at room temperature for 12 hours. The reaction liquid was washed by saturated sodium bicarbonate and water and the organic layer was dried by anhydrous sodium sulfate. The solvent was evaporated and the crude product was crystallized by methanol to give 4.8 g of the title compound, and the yield was 60%. $^1$H NMR (CDCl$_3$): δ 9.47 (s, 1H), 8.22 (dd, 1H), 7.46 (dd, 1H), 8.18-7.44 (m, 5H, H-phenyl), 6.34 (s, 1H), 5.41 (s, 1H,), 4.51-4.66 (m, 2H), 3.62-3.66 (dd, 1H), 3.20-3.23 (dd, 1H), 2.10 (s, 3H).

EXAMPLE 22

The Preparation of Lamivudine and its 5-Position Diastereomer

The compound of Example 21 (3.8 g, 0.01 mol) and 50 ml of methanol were added to a reaction flask, and then $K_2CO_3$ (4.4 g, 0.03 mol) was added. The reaction mixture was reacted at room temperature overnight and filtered. The solvent was evaporated under reduced pressure and the crude product was purified by a silica gel column to give 1.9 g of Lamivudine and its 5-position diastereomer, and the yield was 85%. The ratio of α to β isomers was 1.2:1.

EXAMPLE 23

The preparation of (2R)-5-methoxy-1,3-oxathiolane-2-methyl-(4'-chloro)-benzoate

The compound of formula (VI) (3 g, 0.02 mol), pyridine (3.2 g, 0.04 mol) and 50 ml of dichloromethane were added to a three-necked flask. At room temperature, p-benzoyl chloride (4.1 g, 0.024 mol) was added slowly drop by drop. After the addition was complete, the reaction mixture was reacted at room temperature for 3 hours and then the reaction was stopped. The reaction mixture was filtered and the filtrate was evaporated to dryness to give the title compound, which could be used in the next step without further purification.

EXAMPLE 24

The preparation of (2R,5S)-5-(4"-acetamido-2"-oxo-pyrimidin-1"-yl)-1,3-oxathiolane-2-methyl-(4'-chloro)-benzoate At room temperature, to a solution of the compound from step (1) of Example 15 was added a solution of the compound of Example 23 in dichloromethane (25 ml) and trimethylsilyl triflate (8.9 g, 0.04 mol) and then the reaction mixture was reacted at room temperature for 12 hours. The reaction liquid was washed by saturated sodium bicarbonate and water and the organic layer was dried by anhydrous sodium sulfate. The solvent was evaporated and the crude product was crystallized by methanol to give 5.0 g of the title compound, and the yield was 62%. The ratio of α to β isomers was 1.2:1. $^1$H NMR (CDCl$_3$): δ 9.47 (s, 1H), 8.22 (dd, 1H), 7.46 (dd, 1H), 8.00-7.62 (m, 4H, H-phenyl), 6.34 (s, 1H), 5.41 (s, 1H,), 4.51-4.66 (m, 2H), 3.62-3.66 (dd, 1H), 3.20-3.23 (dd, 1H), 2.10 (s, 3H).

EXAMPLE 25

The Preparation of Lamivudine and its 5-Position Diastereomer

The compound of Example 24 (4.1 g, 0.01 mol) and 50 ml of methanol were added to a reaction flask, and then $K_2CO_3$ (4.4 g, 0.03 mol) was added. The reaction mixture was reacted at room temperature overnight and filtered. The solvent was evaporated under reduced pressure and the crude product was purified by a silica gel column to give 1.9 g of Lamivudine and its 5-position diastereomer, and the yield was 83%. The ratio of a to (3 isomers was 1.2:1.

EXAMPLE 26

The preparation of (2R,5S)-5-(4"-acetamido-2"-oxo-pyrimidin-1"-yl)-1,3-oxathiolane-2-methyl-(2'S-isopropyl-5'R-methyl-1'R-cyclohexyl)-carbonic acid diester of formula (VII)

Under a nitrogen atmosphere, the compound of formula (IV) (16.3 Kg, 49.0 mol), dichloromethane (143.7 L), acetic acid (143.7 L), and acetic anhydride (43.1 L) were added to a reaction flask, and cooled to 0° C., and then a catalytic amount of concentrated sulfuric acid was added dropwise. After the addition was complete, the reaction was conducted at temperature for 1 hour, and then was warmed to room temperature slowly and further reacted for a period (about 2.5 hours). After the reaction was complete, the reaction liquid was poured into ice water and stirred for 30 minutes. The organic layer was separated and washed with saturated sodium bicarbonate aqueous solution and water, and then dried to give a solution of the compound of formula (V) in dichloromethane. The product could be directly used in the next step without further purification.

Under a nitrogen atmosphere, $N^4$-acetylcytosine (9.0 Kg, 58.8 mol), hexamethyldisilazane (15 L) and toluene (28.7 L) were added to a reaction flask, and refluxed for a period, after which, the reaction liquid became clear and was reacted at that temperature for 2 hours, and then was cooled to room temperature to give silylated acetylcytosine solution. To the solution was added a solution of the compound of formula (V) in dichloromethane. After the addition was complete, trimethyliodosilane (16.7 L) was added slowly. After the addition was complete, the reaction mixture was reacted at room temperature for 18 hours. After the reaction was complete, the reaction liquid was poured into an aqueous solution of 10% sodium thiosulfate, and stirred for 1 hour. The organic layer was separated and washed with saturated sodium bicarbonate aqueous solution and water. The solvent was evaporated under reduced pressure. Petroleum ether was added to the residues to precipitate solids, which were filtered to give 14.5 Kg of a mixture of formula (VI), and the yield was 65%. The ratio of α to β isomers was 1:1.6.

The above mixture was added to ethanol (300 L) and refluxed. After the solution became clear, it was cooled to precipitate solids which were then filtered. The step was repeated for twice to thrice to give 2.9 Kg of the title compound, and the yield was 40%.

EXAMPLE 27

The preparation of Lamivudine

The compound of Example 26 (2.9 Kg, 5.4 mol) and methanol (28 L) were added to a reaction flask, and cooled to 0° C., and then $K_2CO_3$ (2.2 Kg, 15.9 mol) was added. The reaction mixture was further stirred for 5 hours. After the reaction was complete, the reaction liquid was filtered and adjusted by concentrated HCl to have a pH of about 4-4.5, and then stirred for 15 minutes, after which it was adjusted by 2M sodium hydroxide solution to have a pH of about 7. The mixture was filtered and methanol was evaporated under reduced pressure from the filtrate. A certain amount of water was added to the residues and then p-nitrobenzoic acid (0.9 Kg, 5.4 mol) was added. Under a nitrogen atmosphere, the mixture wad elevated to a temperature of 70° C., stirred for 30 minutes, cooled, filtered and dried at 45-50° C. in a vacuum drying oven for 8 hours to give a white solid (1.9 Kg), and the yield was 90%.

The resulting salt and ethanol (11 L) were added to a reaction flask. Under a nitrogen atmosphere, the mixture was elevated to a temperature of 70-75° C., and then triethylamine (850 ml) was added slowly. After the addition was complete, the reaction mixture was kept at that temperature under stirring for 0.5 hour. Two thirds of the solvent was evaporated under reduced pressure, and ethyl acetate (5.6 L) was added slowly drop by drop at 50-55° C. After the addition was complete, the mixture was cooled to room temperature, stirred for 5 hours, cooled to 10° C. and then further stirred for 1 hour, after which, the reaction mixture was filtered and the resulting solid was recrystallized by ethanol to give 1.0 Kg of Lamivudine, and the yield was 90%.

The above contents are the basic descriptions of the concept of the present invention, and any equivalent variants made according to the technical solutions of the present invention are within the protection scope of the present invention.

The invention claimed is:

1. A process for stereoselective synthesis of Lamivudine, comprising the following steps:
   (a) performing a glycosylation reaction between the compound of formula (I) and cytosine or protected cytosine, and separating the reaction product by recrystallization to obtain the intermediate of formula (II); and
   (b) deprotecting the intermediate of formula (II) to obtain Lamivudine,
   wherein the reaction scheme is as follows:

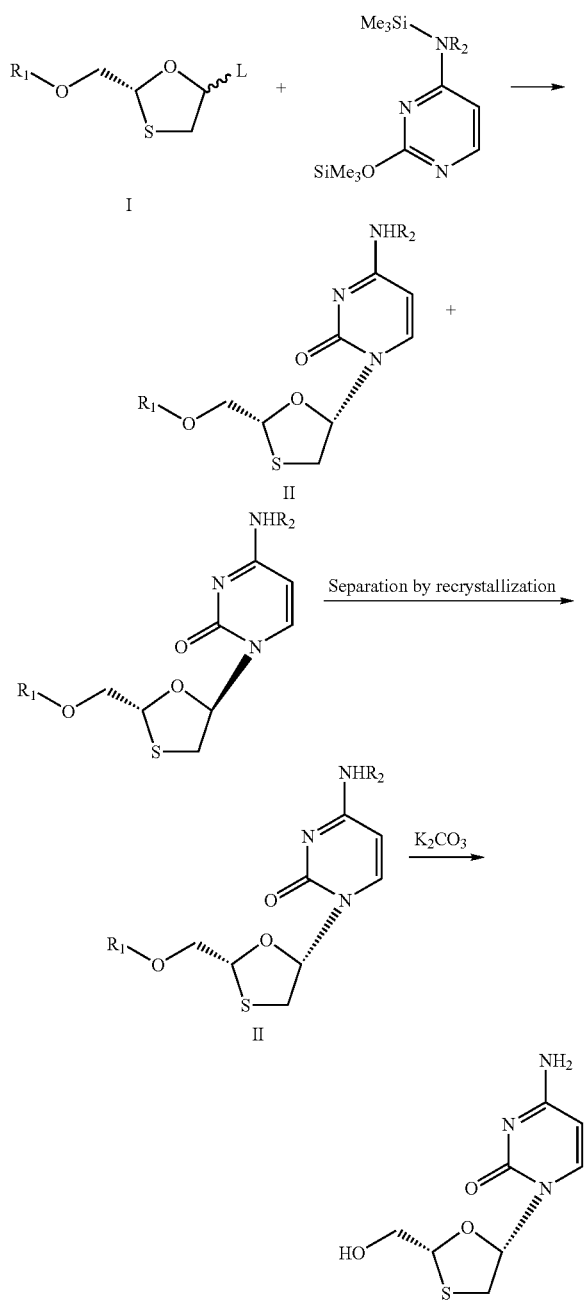

wherein $R_1$ is L-mentholformyl, L is a leaving group; and $R_2$ is a hydrogen or an amino protecting group.

2. The process for stereoselective synthesis of Lamivudine according to claim 1, wherein the preparation method of the compound of formula (I) is as follows: the chiral auxiliary menthol is acylated by triphosgene to give L-menthol chloroformate, which is reacted with 1,2-isopropylidene protected glycerol, and then hydrolyzed to deprotect 1,2-isopropylidene; the resulting product is oxidized by sodium periodate, and condensed with 1,4-dihydroxy-2,5-dithiane to give an intermediate of formula (VIII) of high optical purity; and a hydroxyl at position 5 of the intermediate of formula (VIII) is substituted by chlorine to give a compound of formula (III), which is formula (I) where $R_1$ is L-mentholformyl and L is X; the reaction scheme is as follows:

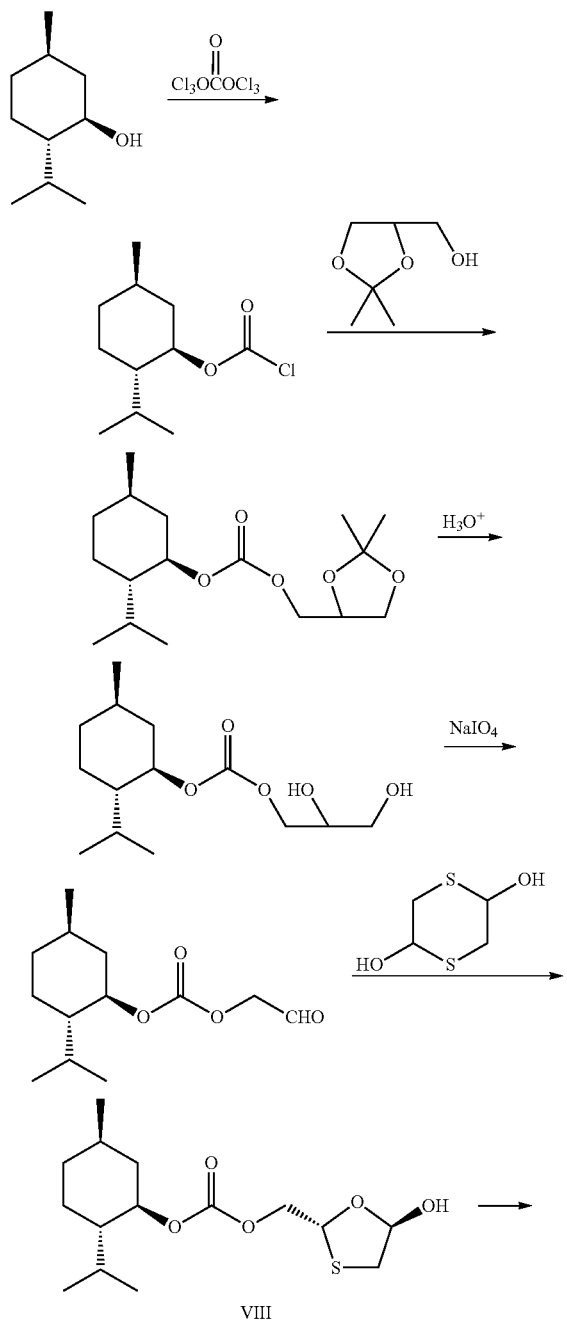

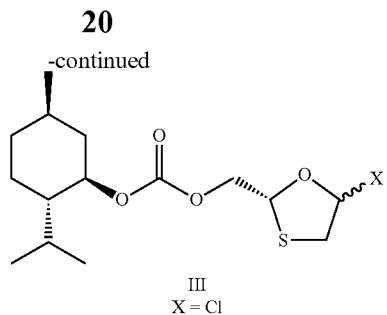

wherein X is Cl.

3. The process for stereoselective synthesis of Lamivudine according to claim 1, wherein the preparation method of the compound of formula (I) is as follows: a chiral compound of formula (IX) is used as a starting material, and methyl etherificated at 5-hydroxy, and then reduced to give the intermediate of formula (X), and then a chiral auxiliary is introduced to the hydroxy at position 2 of the intermediate of formula (X) to obtain the compound of formula (IV), which is formula (I) where $R_1$ is L-mentholformyl and L is methoxy; the reaction scheme is as follows:

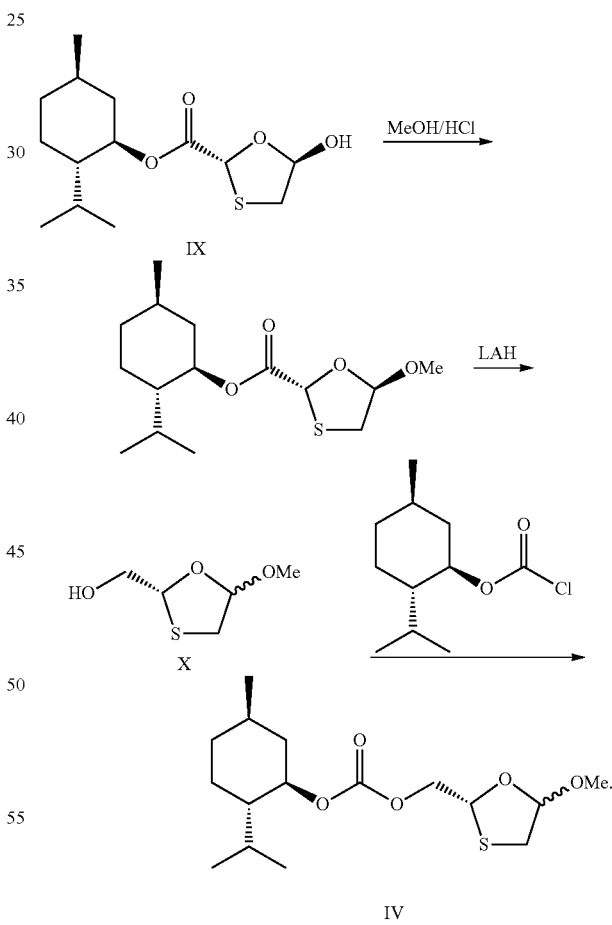

4. The process for stereoselective synthesis of Lamivudine according to claim 3, wherein the intermediate of formula (IV) for chiral control resulting from the compound of formula (X) is transformed to a compound of formula (V), which is formula (I) where $R_1$ is L-mentholformyl and L is acetate, and then undergoes a glycosylation reaction with protected cytosine, and the reaction scheme is as follows:

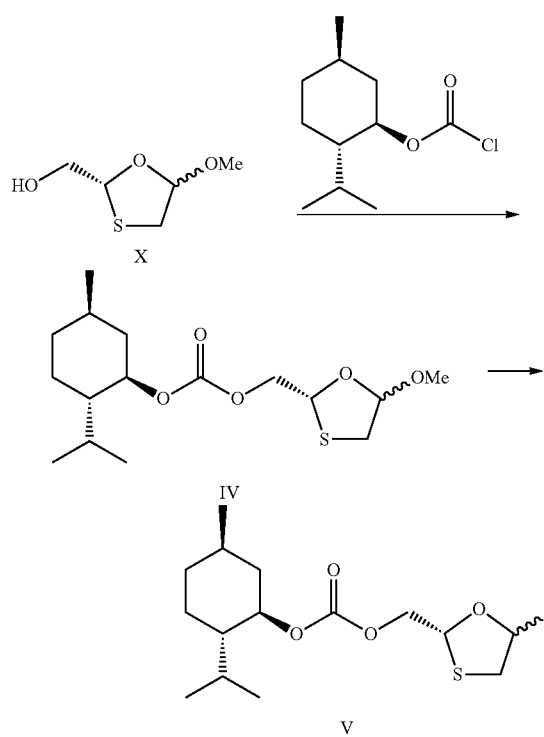

5. The process for stereoselective synthesis of Lamivudine according to claim 1, wherein $R_2$ is hydrogen or acetyl.

6. The process for stereoselective synthesis of Lamivudine according to claim 1, wherein L is methoxy or halogen or acetate group.

7. The process for stereoselective synthesis of Lamivudine according to claim 1, wherein step (a) can be described as follows: cytosine or 4-amino protected cytosine is reacted with hexamethyldisilazane to give silylated 4-amino protected cytosine; which is then reacted with the compound of formula (I) at 10-80° C. for 1-20 hours; finally the resulting glycosylated product is separated by recrystallization to give 2R,5S-intermediate of formula (II) of high optical purity.

8. The process for stereoselective synthesis of Lamivudine according to claim 7, wherein the 4-amino protected cytosine is $N^4$-acetylcytosine.

9. The process for stereoselective synthesis of Lamivudine according to claim 1, 5, 6, or 7, wherein step (b) can be described as follows: the intermediate of formula (II) from step (a) is hydrolyzed by a base, and forms a salt with an organic acid, then the salt precipitates from water and finally the water insoluble salt is neutralized by an organic base to give Lamivudine.

10. The process for stereoselective synthesis of Lamivudine according to claim 9, wherein organic acid is p-nitrobenzoic acid.

11. The process for stereoselective synthesis of Lamivudine according to claim 1, wherein the synthetic scheme is as follows:

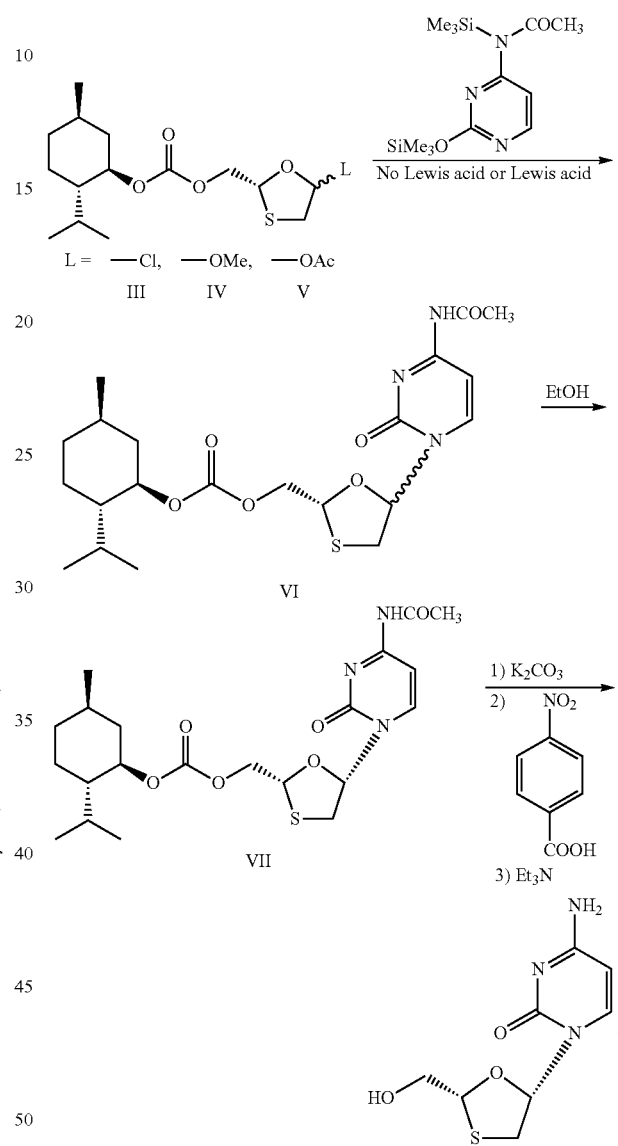

* * * * *